United States Patent [19]

Gault

[11] Patent Number: 5,452,711

[45] Date of Patent: Sep. 26, 1995

[54] SMALL FORM FACTOR ATOMIZER

[75] Inventor: David Gault, Manor, Tex.

[73] Assignee: Exar Corporation, San Jose, Calif.

[21] Appl. No.: 35,679

[22] Filed: Mar. 23, 1993

Related U.S. Application Data

[63] Continuation-in-part of Ser. No. 3,018, Dec. 24, 1992, abandoned.

[51] Int. Cl.$^6$ .................................................. A61M 11/00
[52] U.S. Cl. ................................. 128/200.14; 128/200.16
[58] Field of Search ........................... 128/200.14, 200.16

[56] References Cited

U.S. PATENT DOCUMENTS

| | | | |
|---|---|---|---|
| 4,294,407 | 10/1981 | Reichl et al. | 128/200.16 |
| 4,300,546 | 11/1981 | Kruber | 128/200.16 |
| 4,334,531 | 6/1982 | Reichl et al. | 128/200.16 |
| 4,793,339 | 12/1988 | Matsumoto et al. | 128/200.16 |
| 4,877,989 | 10/1989 | Drews et al. | 128/200.16 |
| 4,976,259 | 12/1990 | Higson et al. | 128/200.16 |
| 4,993,411 | 2/1991 | Callaway | 128/200.16 |
| 5,134,993 | 8/1992 | van der Linden et al. | 128/200.16 |
| 5,152,456 | 10/1992 | Ross et al. | 128/200.16 |

FOREIGN PATENT DOCUMENTS 9217231 10/1992 WIPO .............................. 128/200.23

*Primary Examiner*—Edgar S. Burr
*Assistant Examiner*—Aaron J. Lewis
*Attorney, Agent, or Firm*—Spensley Horn Jubas & Lubitz

[57] ABSTRACT

A reduced form factor atomizer is disclosed comprised of a control electronics module and a dosage/transducer module designed for ultra-compact usage to provide a small and compact form factor. The dosage/transducer module includes a read only memory containing parameters associated with the fluid to be atomized in the module. In use, the two modules are mated together to form the small and compact form factor and include one of a male and female connector to couple the control electronics in the control module to the transducer and the memory in the dosage/transducer module.

6 Claims, 6 Drawing Sheets

SMALL FORM FACTOR ATOMIZER

This application is a continuation in part of my application Ser. No. 29/003,018, filed on Dec. 24, 1992, now abandoned.

BACKGROUND OF THE INVENTION

1. Field of the Invention

This invention relates to an atomizer and more particularly to an atomizer for administering inhalant medicines.

2. Description of the Prior Art

Various medicines are administered by having the patient inhale the drug such as drugs for asthmatics. Commonly, such drugs are in a liquid form where the liquid is broken up into small airborne particles by an atomizer for inhalation.

Conventional medical atomizers use fluoro-carbon gases to break up the liquid into particles. Such fluoro-carbon gas based atomizers are compact and relatively inexpensive.

However, such fluoro-carbon atomizers have several disadvantages. Control of the dosage is difficult as the actual amount of the dosage depends upon atmospheric pressure, atmospheric temperature, the pressure of the gas remaining in the reservoir and the duration of activation of the atomizer.

A far more serious problem with such atomizers is their use of fluoro-carbons. Fluoro-carbons are dangerous pollutants known to destroy the ozone layer of the atmosphere. Because of fluoro-carbons' known pollution effects, the United States government has committed to eliminate all use of fluoro-carbons within the next few years. Therefore, conventional fluoro-carbon atomizers will not be available for administering inhalants within a few years.

There are, of course, other types of atomizers such as ultra-sonic atomizers, air based atomizers, and mechanical atomizers commonly used for personal hygiene products such as deodorants. However, such atomizers have a number of drawbacks. They are typically too large for a person to readily carry them in a shirt pocket or pants pocket. Still further, mechanical atomizers lack control over the dosage of the drug while ultrasonic atomizers are typically quite expensive, costing several hundred dollars a piece.

A typical ultrasonic atomizer will also occupy almost a cubic foot of space and weigh several pounds. Therefore, they are not portable—a critical need for patients such as asthmatics who never know when they may have to administer a particular drug.

Therefore, it is a first object of this invention to have an atomizer providing precise control over the dosage administered to the patient. It is another object of the invention to provide a compact atomizer that does not use fluoro-carbons. It is yet another object of the invention to provide a compact atomizer small enough to place within a typical shirt pocket.

SUMMARY OF THE INVENTION

These and other objects of the invention are accomplished by a two piece ultrasonic atomizer approximately the size of a package of cigarettes; i.e., 3.25 inches by 2.5 inches by 1.2 inches with precise control of the administered dosage.

To achieve this small form factor, the atomizer is divided into two parts: an electronics control module dimensioned 3.25 inches by 1.3 inches by 1.2 inches and a vile/transducer package dimensioned 3.25 inches by 1.2 inches by 1.2 inches. The electronics control package includes as much of the control circuitry as possible using CMOS and BICMOS electronics. The control package also may include a power supply such as batteries and transducers for measuring atmospheric pressure and temperature. In response to these measured parameters, the control electronics provides sufficient excitation of an ultrasonic transducer housed within the dosage/transducer package.

The dosage/transducer module is dimensioned to house a transducer and a programmable read only memory (PROM) providing the stored parameters for use by the control electronics. In addition, the dosage/transducer package also houses a vial containing the liquid medicine. In response to the stored parameters and the measured temperature and pressure, the control electronics excites the transducer for a predetermined time period so that the right amount of the liquid drug is atomized for inhalation by the patient.

Preferably, the dosage/transducer package is disposable and is adapted to engage a dovetail on the electronics control package. There is also an interconnect so that the control electronics are coupled to the PROM and the transducer when the dosage/transducer module is mated to the control module.

DETAILED DESCRIPTION OF THE DRAWINGS

Figure 1:
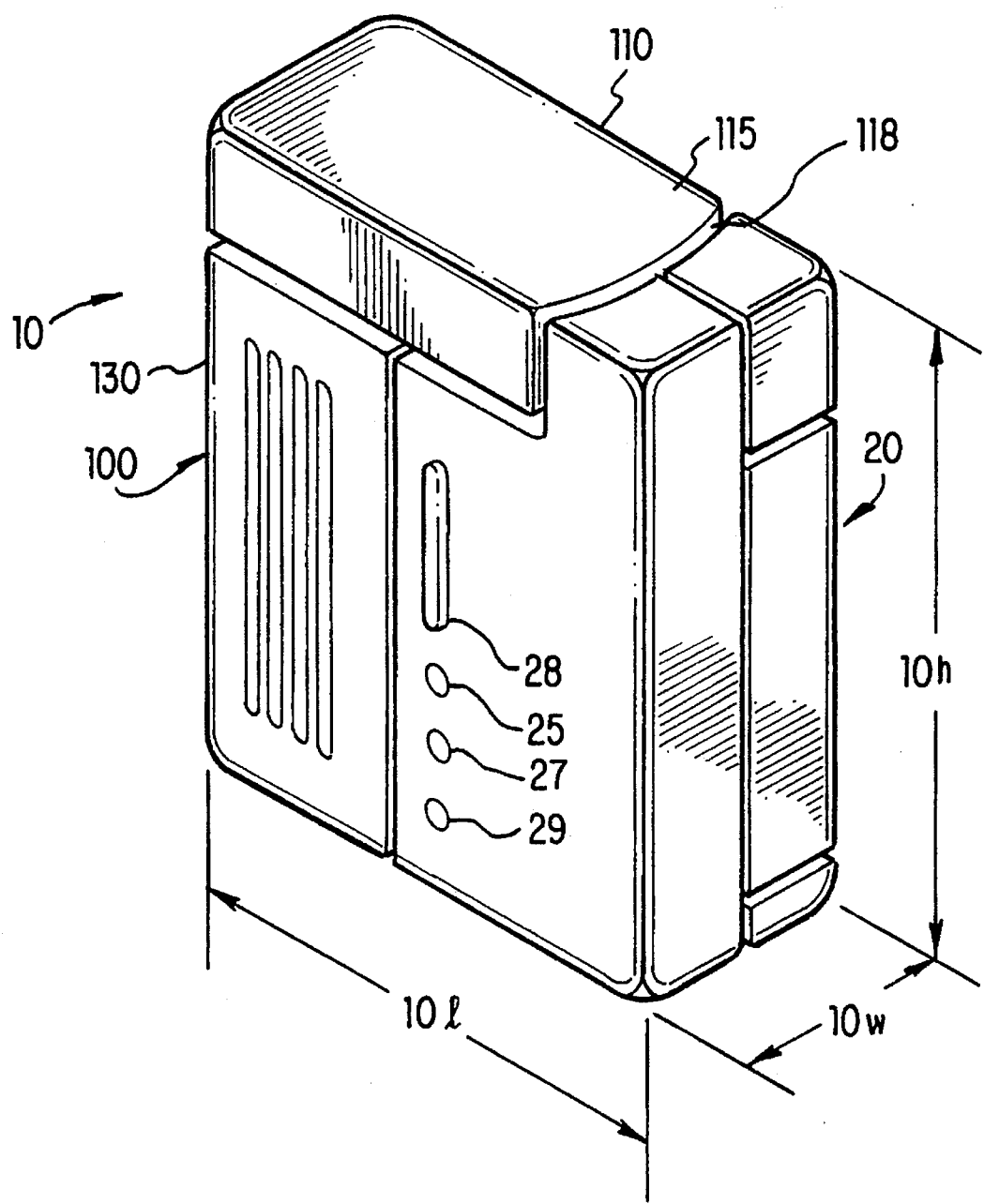
FIG. 1 is a perspective rear view of an embodiment of the invention with the nozzle in the stored position.

FIG. 1 shows a preferred embodiment 10 of the atomizer of the invention. The atomizer is approximately the same size as a package of cigarettes and fits comfortably within a common shirt or pants pocket. In the preferred embodiment 10, the atomizer is dimensioned to be substantially a right parallelepiped having a base that is 2.5 inches long (10 l) by 1.2 inches wide (10 w) and is 3.25 inches high (10 h).

Figure 2:
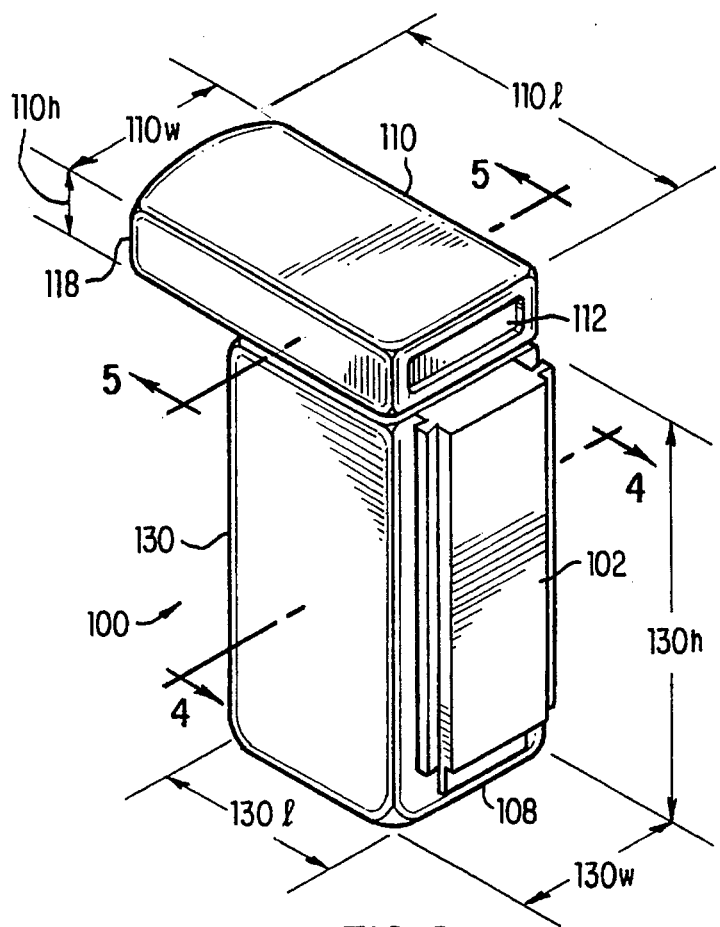
FIG. 2 is a perspective view of the dosage/transducer module of FIG. 1 with the nozzle in the inhaling position.
Figure 3:
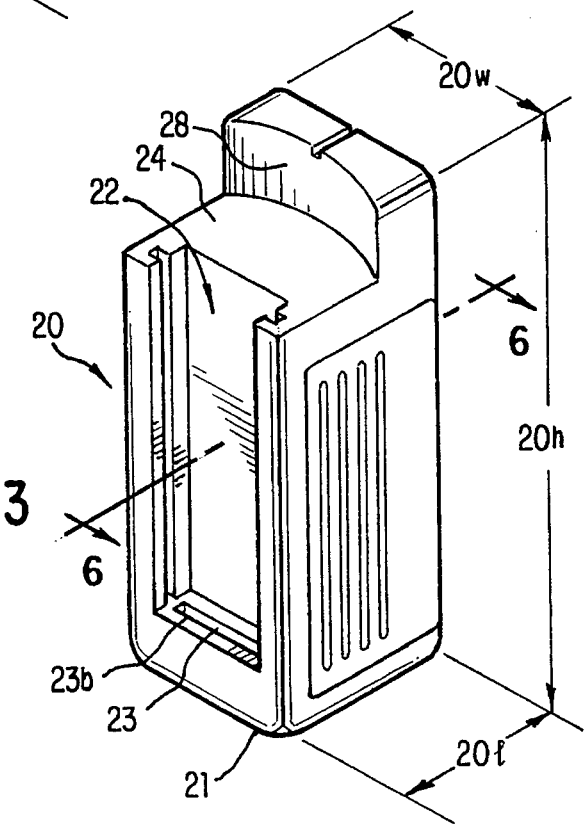
FIG. 3 is a perspective front view of the control electronics module of FIG. 1.

The atomizer 10 comprises two parts: a control electronics module 20 and a dosage/transducer module 100. Referring to FIG. 2 and 3, it can be seen that the two modules 20, 100 slidably engage by using a dovetail male member 102 on the dosage/transducer module 100 and a female cavity 22 defined by the control electronics module 20. When the two modules 20, 100 are mated together as shown in FIG. 1, a card edge connector 108 engages the connector socket 23b contained within a cavity 23 at an end of the female cavity 22 that is 20 hundredths of an inch deep.

Figure 4:
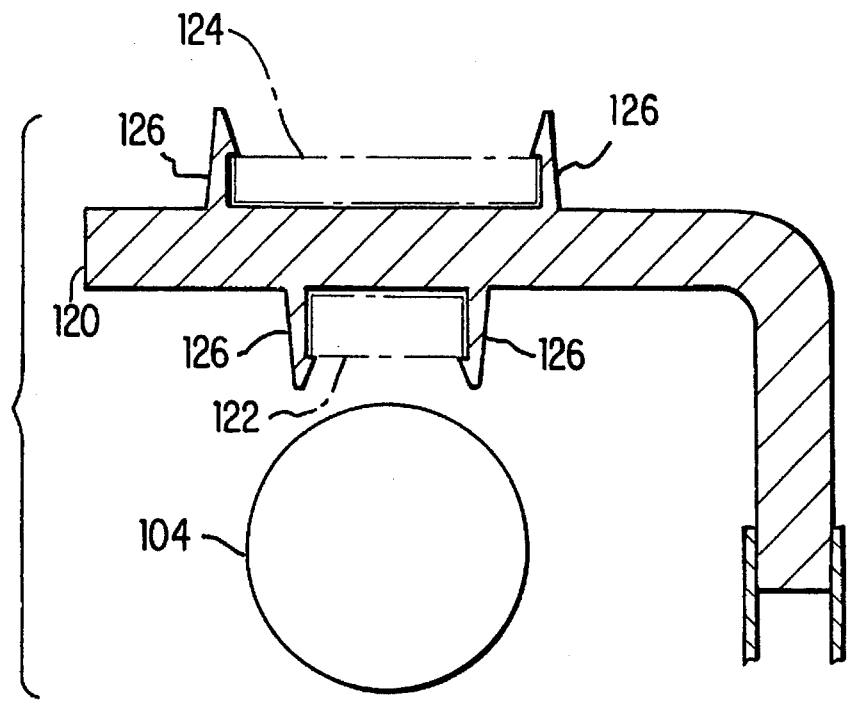
FIG. 4 is a partial sectional view of the dosage/transducer module taken along line 4—4 in FIG. 2.
Figure 5:
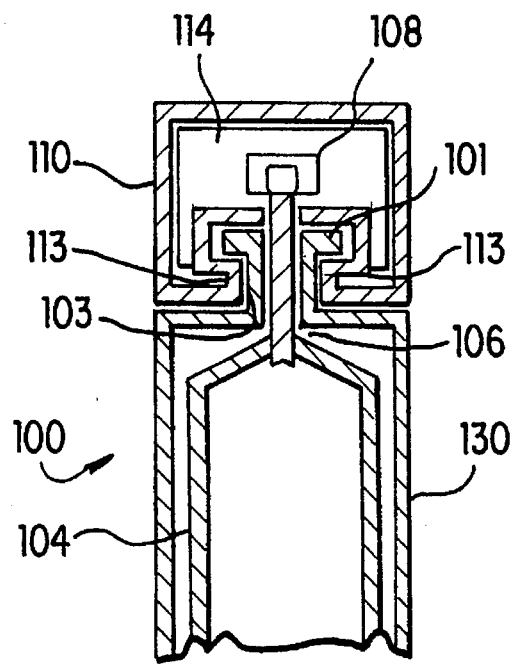
FIG. 5 is a partial sectional view of the dosage/transducer module taken along line 5—5 in FIG. 2.

The dosage/transducer module 100 also includes a rotatable nozzle 110 that may be pivoted through a one hundred eighty degree arc from a closed or stowed position (FIG. 1) to an opened or inhaling position (FIG. 2). The nozzle 110 defines an outlet 114 (FIG. 5) and defines an inlet 112 (FIG. 2) communicating with the outlet and through a check valve 108 and a tube 106 with the interior of a vial 104 containing medicine (FIG. 5). To use the atomizer, the patient presses the start button 28 (FIG. 2) and the control module 20 activates an ultrasonic transducer 124 (FIG. 4) mounted in the dosage/transducer module 100. Once the appropriate quantity of the fluid contained in the vial 104 (FIG. 5) has been atomized, the ultrasonic transducer 124 is deactivated and the patient may inhale the atomized fluid by sucking at the outlet port 114.

The dosage/transducer module 100 comprises two separate parts: a base 130 and the nozzle 110. As can be seen in FIGS. 2 and 4, the base 130 houses the printed circuit board 120, the connector 108 and the vial 104. To save space, a PROM 122 and the transducer 124 are surface mounted devices held in place by snap lock assemblies 126 coupled to the board 120 as shown in FIG. 4. Also coupled to circuitry on the printed circuit board 120 by wires (not shown) is a male card edge connector member 108 disposed at the bottom end of the dovetail male member 102. The exterior of the base 130 may be comprised of plastic injected molded parts that are assembled by force fitting the parts together. During assembly, the printed circuit board 108, the male connector member 108 and the vial 104 may be forced into clips or slots (not shown) defined in the interior sides, bottom and top of the base 130.

At the top of the base 130, a collar 101 is formed. Except for this collar 101, the base 130 is substantially a right parallelepiped that is dimensioned 1.2 inches long (130 l) by 1.2 inches wide (130 w) by 2.76 inches high (130 h). The base is preferably configured so that the interior is dimensioned no larger than to contain the vial 104 and the transducer 124. The vial is preferably dimensioned to a have a diameter of about 1.1 inches and a height of about 1 inch.

The nozzle 110 is also shaped substantially as a right parallelepiped dimensioned 1.89 inches long (110 l) by 1.2 inches wide (110 w) by 0.49 inches high (110 h) except for a curved surface by the outlet 114 and fits atop the base 130. The nozzle 110 has a circular flange 113 designed to be forced during assembly to sit within a groove 103 defined by the collar 101 so that the nozzle 110 may rotate freely after assembly. A pipe 106 communicates from the upper interior of the vial 104 to a check valve 108 mounted in the nozzle 110 and normally in the closed position. When the patient sucks on the nozzle 110 at the opening 114, the resultant partial vacuum is sufficient to open the valve 108 to permit the atomized fluid in the vial to be evacuated and inhaled by the patient. Baffles (not shown) may also be included within the interior of the nozzle 110 to limit air flow through the nozzle 110.

The control module 20 is dimensioned to be a right parallelepiped that is 3.25 inches high (20 h) by 1.3 inches long (20 l) by 1.2 inches wide (20 w) except for a cutout 24 conforming to the shape of part of the nozzle 110 so that the entire embodiment 10 forms a right parallelepiped when the nozzle is stowed (FIG. 1). The cutout portion 24 is 0.69 inches long by 1.2 inches wide by 0.49 inches high and has a curved surface 28 to match the curved surface 118 of the nozzle 110. The control module has on a surface the start switch 28 for activating the embodiment 10, and a normal light emitting diode (LED) 25, a low battery LED 27 and a low dose LED 29. These LEDs indicate to a user respectively when the unit is functioning normally, when the batteries 26 need to be replaced and when the dosage/transducer module 100 needs to be replaced. The control module also defines at an end of the female cavity 22 a connector cup 21. The connector cup 21 defines a connector opening 23 within which is housed a edge connector socket 23.

Figure 6:
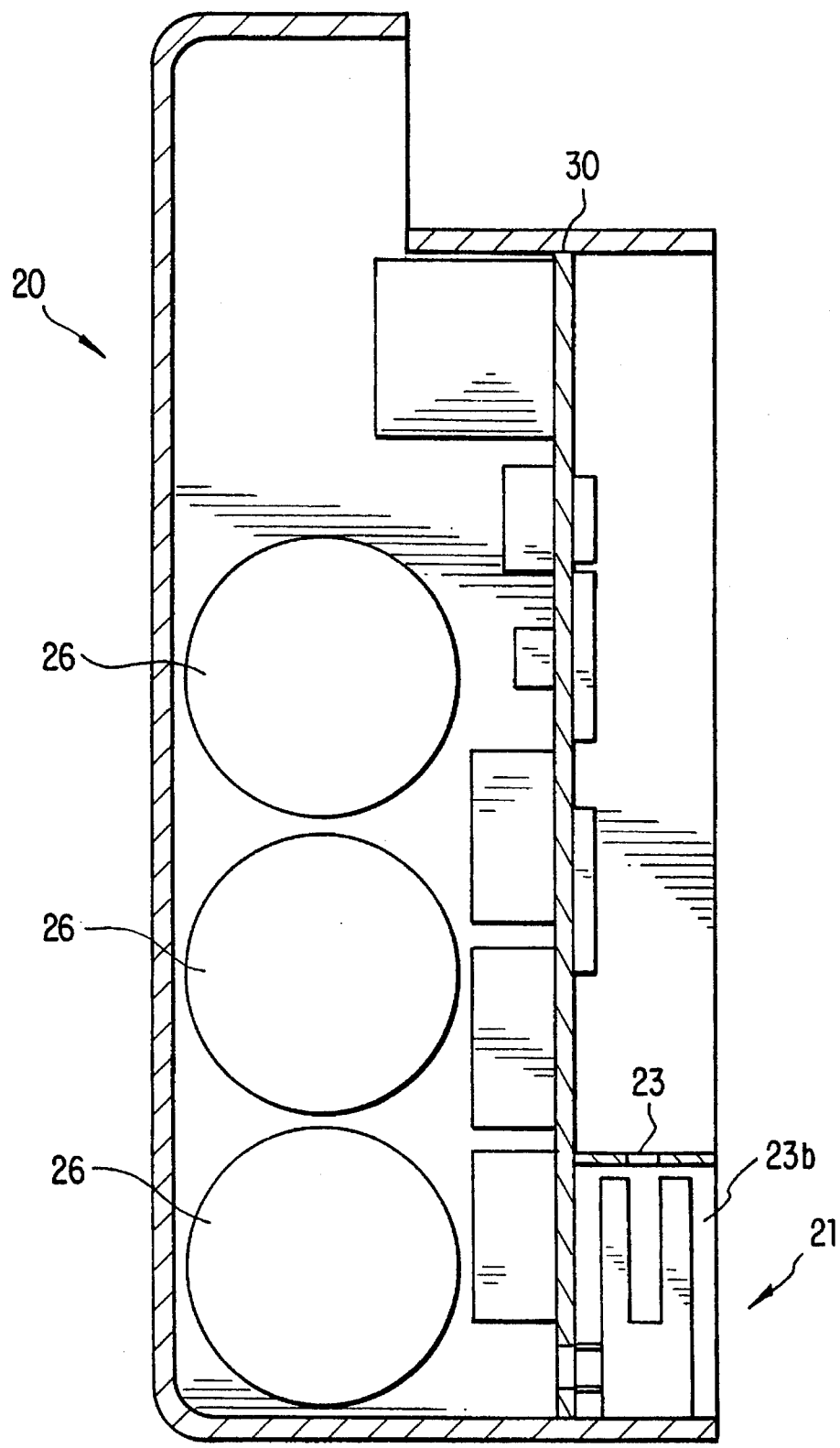
FIG. 6 is a sectional view of the control electronics module of FIG. 3 taken along line 6—6.

FIG. 6 shows a cross section of the control module 20. The control module 20 includes a printed circuit board 30 upon which all of the electronics components are mounted except for the ultrasonic transducer 124, the PROM 122, the level sensor 126 and an optional atomization sensor (not shown). To reduce the overall size of the unit, where possible, all circuit elements use low profile, surface mount components. In addition to the electronic components, the module 20 also includes three AA Ni-Cad batteries 26. A removable battery cover (not shown) may be included to permit easy replacement of exhausted batteries.

The sides of the control module 20 may be made of a high impact plastic and may be assembled by snapping the parts together. Batteries 20, the circuit board 30 and the connector 23b may be mounted during assembly in clips or slots (not shown) defined on the interior walls of the module 20.

Figure 7A:
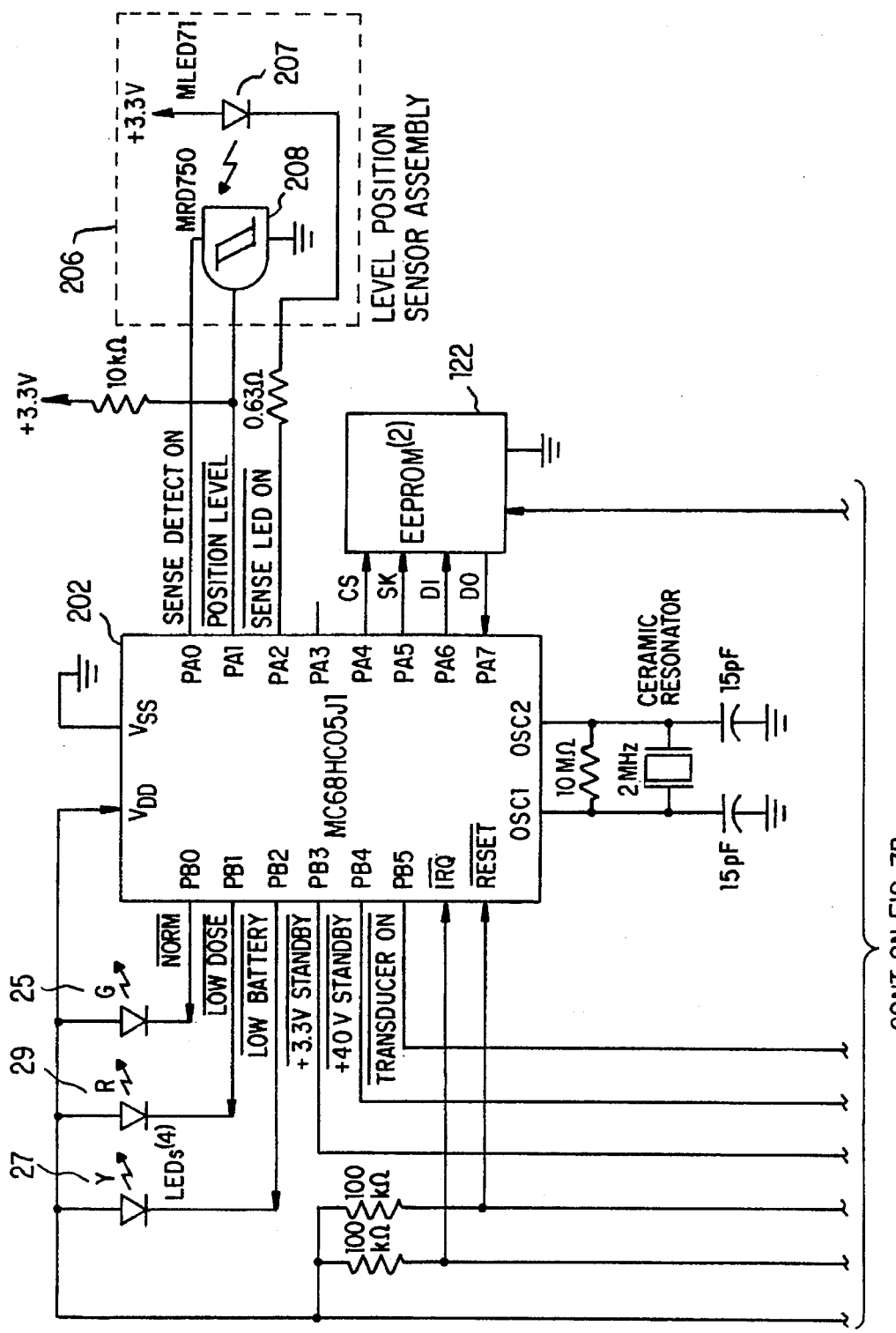
FIG. 7 is a schematic for the circuitry of the embodiment of FIG. 1.
Figure 7B:
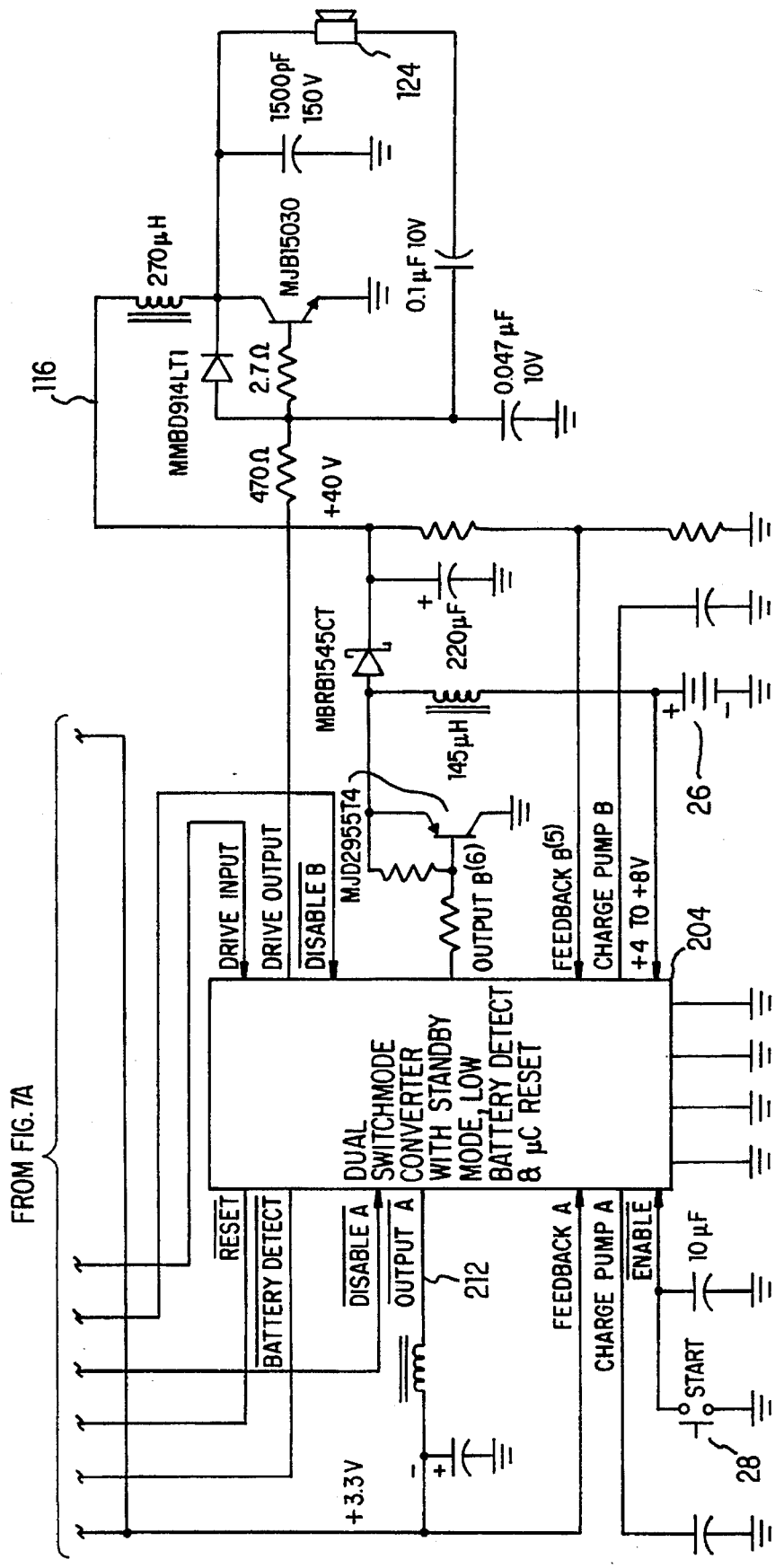

FIG. 7 shows a schematic of the electronics of the package 20. The two principal components are a microcontroller 202 and a hybrid integrated circuit 204. The microcontroller 202 may be a CMOS MC6809 available from Motorola and is coupled to a level position sensor assembly 206 at port PA. Additional sensors such as a temperature sensor (not shown), a pressure sensor (not shown) and a atomization sensor (not shown) may also be coupled to additional ports of the microcontroller 202. The level position sensor 206 comprises an LED 207 and a Schmitt trigger gate 205 that indicate when the level in the vial 104 has fallen below a predetermined level. In response to that condition occurring, the microcontroller 202 through port PB1 activates the low dose LED 20. In addition, depending upon the specific drug involved and the associated parameters stored in the PROM 122, in response to a low fluid level being sensed, the entire embodiment 10 may be disabled until the dosage/transducer module 100 is replaced.

The hybrid integrated circuit 204 is a BiCMOS part to conserve power and includes dual charge pumps both of which may be switched into a standby mode for power conservation. The hybrid circuit 204 also includes a battery level detection circuit and a micro-controller reset circuit. The charge pumps are used for DC to DC conversion to supply the different biasing voltages required by the circuitry.

In response to depression of the start switch 28, the hybrid integrated circuit 204 is activated and switches charge pump voltage converter A from standby to active mode. At that point, Output A 212 provides a 3.3 volt Vcc voltage to both the PROM 122 and the micro-controller 202. The voltage is also monitored by the hybrid circuit 204 at the input feedback A. Once the voltage has stabilized, the hybrid circuit 204 resets the microcontroller 202 by providing a low signal on the Reset* signal.

After being reset, the microcontroller 202 interrogates the level position sensor assembly 206, the temperature sensor (not shown) and the pressure sensor (not shown) and the PROM 122. If the position level sensor 206 indicates that the fluid level in the vial 104 is below the prescribed minimum level, a low dose LED 29 is turned on and the +3.3 volt standby* signal is generated to deactivate charge pump converter A in the hybrid circuit 204. Otherwise, the green LED 25 is lit to indicate that the embodiment 10 is functioning properly.

If the fluid level is sufficient, using the +40 volt standby* signal, the microcontroller 202 will activate the charge pump converter B to provide at output B a forty volt DC bias level. This forty volt level is monitored at feedback B. After measuring the temperature and atmospheric pressure, the microcontroller 202 will turn on the ultrasonic transducer 124 by signalling on the transducer on* signal providing a sine wave at a frequency of 1.7 Megahertz to the amplifier 116. The amplifier in turn drives the transducer 124 with a 100 volt peak-to-peak signal to atomize the fluid.

Based upon the stored information in the PROM 122 and the sensed temperature and pressure, the microcontroller causes the transducer to be activated for a predetermined time interval stored in the PROM 122 to atomize the proper dosage of the medicine in the vial 104. Once that time interval has ended, the microcontroller 202 may deactivate the transducer through the transducer on* signal. The appropriate data for the time interval of activation of the ultrasonic transducer 124 may be experimentally determined based upon the desired dosage and varying the temperature and the pressure. Based upon the measured data, a look-up table for the appropriate parameters may then be stored in the PROM 122.

Alternatively, the microcontroller 202 may monitor an atomization transducer (not shown) that determines when a light beam is blocked or a sufficient amount of light from a light beam is reflected by the atomized fluid that a sufficient amount of the fluid has been atomized. Either in response to the atomization transducer or the passage of time, the microcontroller 202 deactivates the two charge pumps through the 3.3 volt standby* and the 40 volt standby signals to conserve power. Once the dosage has been atomized, the user may suck at the outlet 112, providing sufficient pressure to open the check valve (not shown) and inhale the atomized drug.

In addition, the battery detection circuitry in the hybrid circuit 204 monitors the voltage across the batteries 26. When the battery voltage drops below a predetermined level as measured according to any of the well known algorithms for monitoring Ni-Cad batteries, the hybrid circuit will activate the battery detect* signal to cause the microcontroller 202 to activate the low battery LED 27. In response to the low voltage condition, the hybrid circuit 204 may prevent the embodiment 10 from operating until the batteries are replaced or re-charged.

Similarly, in response to the low dosage light being lit, the patient may replace the dosage/transducer module with a fresh module 100 containing a full vial 104. The dosage/transducer modules 100 may be made of a high temperature plastic so that before replacement of the vial, the module 100 may be sterilized for subsequent reuse. To replace the dosage/transducer module 100, the patient presses against the dosage/transducer module 100 in one direction and the control module 20 in the other direction. The male card connector 108 and the female socket 23b disconnect and the dovetail 102 is slid out of the female cavity 22 until the two modules are separated. A new dosage/transducer module 100 is then positioned so that the dovetail male member 102 adjacent to a card edge connector 108 is positioned to engage the female cavity 22. The two modules 20 and 100 are slid with respect to each other until the terminals of the card edge connector 108 affirmatively engage the terminals 23b of the edge connector socket to electrically couple the circuitry of the modules 20 and 100 together. When mated, the two modules 20 and 100 form a package dimensioned 3.25 inches by 2.5 inches by 1.2 inches.

In the particular embodiment 10, the width of both modules 20, 100, is designed to just be slightly bigger than the diameter of the transducer 124. This permits an ultracompact atomizer much smaller and lighter than conventional atomizers.

Although a specific embodiment 10 is shown, it would be understood by those of ordinary skill that the same principles may be applied to other embodiments. For example instead of using a card edge connector, a connector made according to DIN41612 Standard for Euro-connectors, Military Standard MIL-C-55302 connectors, pin and socket type connectors, and dip solder connectors may be used. Similarly, other types of mating mechanisms other than a tongue and groove assembly may be used to mate the two modules 20, 100 together such as other common variants of tongue and groove and mortise and tenon based locking mechanisms besides a dovetail. Resort to the true scope of the invention should be had by resort to the claims.

I claim:

1. A compact atomizer assembly comprising:
   a transducer module including:
   a vial containing a fluid to be atomized;
   an ultrasonic transducer positioned to couple ultrasonic energy to the fluid in the vial for atomizing at least a portion of the fluid in the vial;
   a first connector member having a plurality of first terminals, at least two of said terminals being operatively coupled to the transducer; and
   a transducer/vial housing containing the vial, the transducer and at least a part of the connector member and the housing including a transducer module mating means; and
   a control module including control module mating means positioned to engage the transducer module mating means for forming a common computer assembly, the control module comprising:
   a battery power source;
   a control circuit to activate the ultrasonic transducer in a predetermined manner; and
   a second connector member having a plurality of terminals positioned to electrically connect the control circuit to the transducer when the two modules are mated.

2. The atomizer assembly of claim 1, wherein when the control module and the transducer module terminals are electrically connected, the entire assembly occupies a volume less than or equal to about 3.25 inches by 1.3 inches by 1.2 inches.

3. The atomizer assembly of claim 1, wherein the dosage/transducer housing further includes a rotatable nozzle having an interior communicating via a tube with the interior of the vial and the nozzle defining an opening for inhaling the atomized fluid from the atomizer.

4. The atomizer assembly of claim 1, wherein the nozzle further includes an air inlet.

5. The atomizer assembly of claim 1, wherein said transducer module further includes a male connector and said control module further includes a female connector, the male connector comprises a printed circuit board having adjacently positioned terminal elements and the female connector comprises a card edge socket.

6. A method for atomizing a fluid contained in a vial positioned next to an ultrasonic transducer contained within a first module, the first module also including a read only memory storing parameters relating to the atomization of the fluids and a second, separate module containing control electronics, the method comprising:

coupling the modules together such that terminals of the first module are electrically coupled to terminals of the second module;

activating a switch;

reading the parameters from the read only memory in the first module and providing them through a terminal to the control electronics in the control module;

activating the transducer through terminals for a period of time based at least in part upon the parameters obtained from the read only memory to atomize the fluid in the vial; and sucking the fluid from the vial.

* * * * *